United States Patent
Kato

(10) Patent No.: US 11,479,641 B2
(45) Date of Patent: Oct. 25, 2022

(54) FLUORINE-CONTAINING ETHER COMPOUND, LUBRICANT FOR MAGNETIC RECORDING MEDIUM, AND MAGNETIC RECORDING MEDIUM

(71) Applicant: SHOWA DENKO K.K., Tokyo (JP)

(72) Inventor: Tsuyoshi Kato, Ichihara (JP)

(73) Assignee: SHOWA DENKO K.K., Tokyo (JP)

( * ) Notice: Subject to any disclaimer, the term of this patent is extended or adjusted under 35 U.S.C. 154(b) by 294 days.

(21) Appl. No.: 16/640,145

(22) PCT Filed: Aug. 7, 2018

(86) PCT No.: PCT/JP2018/029568
§ 371 (c)(1),
(2) Date: Feb. 19, 2020

(87) PCT Pub. No.: WO2019/039265
PCT Pub. Date: Feb. 28, 2019

(65) Prior Publication Data
US 2021/0155751 A1   May 27, 2021

(30) Foreign Application Priority Data
Aug. 21, 2017 (JP) .............................. JP2017-158651

(51) Int. Cl.
*C08G 65/22* (2006.01)
*C08G 65/333* (2006.01)
*G11B 5/725* (2006.01)

(52) U.S. Cl.
CPC ......... *C08G 65/226* (2013.01); *C08G 65/333* (2013.01); *G11B 5/7257* (2020.08)

(58) Field of Classification Search
CPC ........ C10M 107/38; C10M 2213/0606; C10M 105/54; C10M 2213/06; C10N 2040/18;
(Continued)

(56) References Cited

U.S. PATENT DOCUMENTS

| 5,959,058 A | 9/1999 | Tonelli et al. |
| 6,187,954 B1 | 2/2001 | Falcone |

(Continued)

FOREIGN PATENT DOCUMENTS

| JP | 05-247200 A | 9/1993 |
| JP | 08-259882 A | 10/1996 |

(Continued)

OTHER PUBLICATIONS

International Search Report of PCT/JP2018/029568 dated Nov. 6, 2018 [PCT/ISA/210].

*Primary Examiner* — Vishal V Vasisth
(74) *Attorney, Agent, or Firm* — Sughrue Mion, PLLC

(57) ABSTRACT

A fluorine-containing ether compound characterized by being represented by the following formula (1):

$$R^1-R^2-CH_2-R^3-CH_2-R^4-R^5 \qquad (1)$$

In the formula (1), $R^3$ is a perfluoropolyether chain. $R^2$ and $R^4$ are divalent linkage groups having a polar group and may be the same or different. $R^1$ and $R^5$ are bonded to an atom other than a carbon atom of $R^2$ or $R^4$. $R^1$ and $R^5$ are terminal groups composed of an organic group having 1 to 8 carbon atoms and may be the same or different. At least one of $R^1$ and $R^5$ is a chain organic group having 1 to 8 carbon atoms wherein one or more hydrogen atoms of the chain organic group is substituted with a group having an amide bond.

10 Claims, 1 Drawing Sheet

(58) Field of Classification Search
CPC ............ C10N 2030/06; C10N 2020/04; C10N 2050/023; C10N 2050/025; C08G 65/007; C08G 65/333; C08G 65/331; C08G 65/226; C08G 65/329; G11B 5/725; G11B 5/7266; G11B 5/7257; C07C 43/1786; C07C 233/25
See application file for complete search history.

(56) References Cited

U.S. PATENT DOCUMENTS

2013/0209837 A1\* 8/2013 Sagata .................. G11B 5/725
 428/833
2015/0371672 A1 12/2015 Sagata

FOREIGN PATENT DOCUMENTS

| | | |
|---|---|---|
| JP | 09-255608 A | 9/1997 |
| JP | 4632144 B2 | 2/2011 |
| JP | 2013-163667 A | 8/2013 |
| WO | 2015/087615 A1 | 6/2015 |

\* cited by examiner

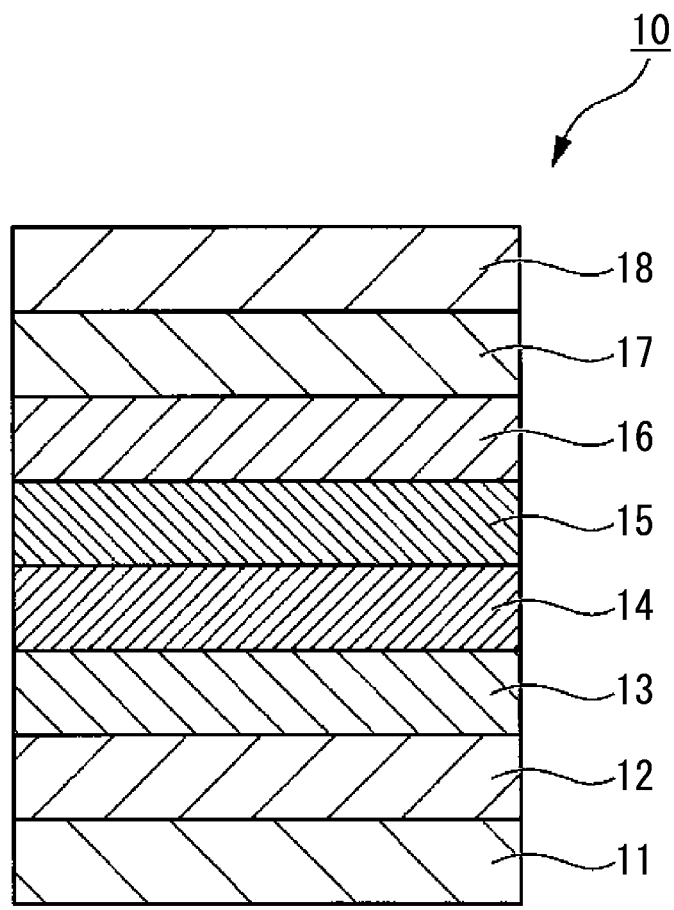

FLUORINE-CONTAINING ETHER COMPOUND, LUBRICANT FOR MAGNETIC RECORDING MEDIUM, AND MAGNETIC RECORDING MEDIUM

CROSS REFERENCE TO RELATED APPLICATIONS

This application is a National Stage of International Application No. PCT/JP2018/029568, filed Aug. 7, 2018, claiming priority to Japanese Patent Application No. 2017-158651, filed Aug. 21, 2017, the contents of all of which are incorporated herein by reference in their entirety.

BACKGROUND OF THE INVENTION

Field of the Invention

The present invention relates to a fluorine-containing ether compound suitable for use as a lubricant for magnetic recording media, a lubricant for magnetic recording media containing the same, and a magnetic recording medium.

BACKGROUND

In recent years, as information processing capacity increases, various information recording technologies have been developed. In particular, a magnetic recording medium suitable for high recording density has been developed.

Conventionally, in a magnetic recording medium, a protective layer and a lubricant layer are provided on the magnetic recording layer formed on the substrate in order to ensure the durability and reliability of the magnetic recording medium. In particular, various characteristics such as long-term stability, chemical substance resistance (preventing contamination such as siloxane) and wear resistance are required for the lubricant layer used for the outermost surface.

Conventionally, as a lubricant for a magnetic recording medium, a perfluoropolyether lubricant having a polar group at a terminal of a molecule has been used in many cases.

As the perfluoropolyether-based lubricant, for example, a perfluoropolyether compound having a terminal group which includes a plurality of hydroxy groups is known (for example, see Patent Document 1). In addition, a lubricant containing a fluoropolyether compound having an aromatic group and a hydroxyl group is known (see, for example, Patent Document 2).

PATENT DOCUMENT

[Patent Document 1] Japanese Patent No. 4632144
[Patent Document 2] Japanese Unexamined Patent Application, First Publication No. 2013-163667

SUMMARY OF THE INVENTION

In recent years, as the information recording density of a magnetic disk rapidly increases, it has been required to reduce the magnetic spacing between the magnetic head and the recording layer of the magnetic disk. For this reason, it is necessary to further reduce the thickness of the lubricant layer existing between the magnetic head and the recording layer of the magnetic disk. The lubricant used for the lubricant layer has a great influence on the reliability of the magnetic disk. Therefore, it is necessary to reduce the thickness of the lubricant layer while ensuring reliability such as wear resistance which is essential for the magnetic disk.

In addition, the environmental resistance requirements for magnetic disks have become very stringent due to diversification of applications of magnetic disks. For this reason, it is required to improve the wear resistance and chemical substance resistance of the lubricant layer, which greatly affects the reliability of the magnetic disk, over those of the prior art.

However, generally, when the thickness of the lubricant layer is reduced, the coverage is reduced, and the chemical substance resistance and the wear resistance tend to deteriorate.

The present invention has been made in view of the above circumstances, and an object of the present invention is to provide a fluorine-containing ether compound capable of forming a lubricant layer having excellent chemical substance resistance and wear resistance even when the thickness is small, which can be suitably used as a material for a lubricant for a magnetic recording medium.

Another object of the present invention is to provide a lubricant for magnetic recording medium containing the fluorine-containing ether compound of the present invention.

Another object of the present invention is to provide a magnetic recording medium having a lubricant layer containing the fluorine-containing ether compound of the present invention.

The present inventors have conducted extensive research to solve the above problems.

As a result, the inventors have found that a fluorine-containing ether compound can be used, in which a divalent linkage group having a polar group is linked to both terminals of a perfluoropolyether chain, and a terminal group, which is a chain organic group having 1 to 8 carbon atoms wherein one or more hydrogen atoms of the chain organic group is substituted with a group having an amide bond, is bonded to at least one of the linkage groups.

That is, the present invention relates to the following matters.

[1] A fluorine-containing ether compound represented by the following formula (1).

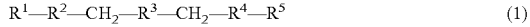

$$R^1-R^2-CH_2-R^3-CH_2-R^4-R^5 \quad (1)$$

wherein in the formula (1), $R^3$ is a perfluoropolyether chain; $R^2$ and $R^4$ are divalent linkage groups having a polar group and may be the same or different; $R^1$ and $R^5$ are bonded to an atom other than a carbon atom of $R^2$ or $R^4$; $R^1$ and $R^5$ are terminal groups composed of an organic group having 1 to 8 carbon atoms and may be the same or different; and at least one of $R^1$ and $R^5$ is a chain organic group having 1 to 8 carbon atoms wherein one or more hydrogen atoms of the chain organic group is substituted with a group having an amide bond.

[2] The fluorine-containing ether compound according to [1], wherein the chain organic group is an alkyl group having 1 to 4 carbon atoms.

[3] The fluorine-containing ether compound according to [1] or [2], wherein the polar group is a hydroxy group.

[4] The fluorine-containing ether compound according to any one of [1] to [3], wherein $R^2$ and $R^4$ in the formula (1) are the following formula (2-1).

$$-(O-CH_2CH(OH)CH_2)_a-O- \quad (2-1)$$

In the formula (2-1), a represents an integer of 1 to 3.

[5] The fluorine-containing ether compound according to any one of [1] to [4], wherein in the formula (1), $R^1$ is a chain organic group having 1 to 8 carbon atoms wherein one or more hydrogen atoms of the chain organic group are substituted with a group having an amide bond, and $R^5$ is an alkyl group in which one or more hydrogen atoms are substituted with a polar group.

[6] The fluorine-containing ether compound according to any one of [1] to [5], wherein in the formula (1), $R^3$ is any one of the following formulas (3) to (5).

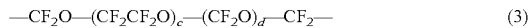

$$—CF_2O—(CF_2CF_2O)_c—(CF_2O)_d—CF_2— \quad (3)$$

In the formula (3), c and d represent an average degree of polymerization and each represents 0 to 20, provided that c or d is 0.1 or more.

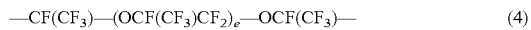

$$—CF(CF_3)—(OCF(CF_3)CF_2)_e—OCF(CF_3)— \quad (4)$$

In the formula (4), e represents an average degree of polymerization and represents 0.1 to 20.

$$—CF_2CF_2—(OCF_2CF_2CF_2)_f—OCF_2CF_2— \quad (5)$$

In the formula (5), f represents an average degree of polymerization and represents 0.1 to 20.

[7] The fluorine-containing ether compound according to any one of [1] to [6], wherein a number average molecular weight is in the range of 500 to 10,000.

[8] A lubricant for magnetic recording media comprising the fluorine-containing ether compound according to any one of [1] to [7].

[9] A magnetic recording medium in which at least a magnetic layer, a protective layer, and a lubricant layer are sequentially provided on a substrate, wherein the lubricant layer contains the fluorine-containing ether compound according to any one of [1] to [7].

[10] The magnetic recording medium according to [9], wherein an average film thickness of the lubricant layer is 0.5 nm to 2 nm.

The fluorine-containing ether compound of the present invention is suitable to be used as a material for a lubricant for magnetic recording media. Since the lubricant for magnetic recording media of the present invention contains the fluorine-containing ether compound of the present invention, a lubricant layer having excellent chemical substance resistance and wear resistance can be formed even if the thickness is small.

Since the magnetic recording medium of the present invention has a lubricant layer having excellent chemical substance resistance and wear resistance, it is excellent in reliability and durability.

BRIEF DESCRIPTION OF THE DRAWINGS

FIG. 1 is a schematic cross-sectional view showing an embodiment of a magnetic recording medium of the present invention.

DETAILED DESCRIPTION OF THE INVENTION

Hereinafter, the fluorine-containing ether compound, the lubricant for magnetic recording media (hereinafter sometimes referred to as "lubricant") and the magnetic recording medium of the present invention will be described in detail. This invention is not limited only to embodiments shown below.

[Fluorine-Containing Ether Compound]

The fluorine-containing ether compound of this embodiment is represented by the following formula (1).

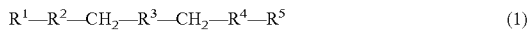

$$R^1—R^2—CH_2—R^3—CH_2—R^4—R^5 \quad (1)$$

In the formula (1), $R^3$ is a perfluoropolyether chain. $R^2$ and $R^4$ are divalent linkage groups having a polar group and may be the same or different. $R^1$ and $R^5$ are bonded to an atom other than the carbon atom of $R^2$ or $R^4$; R and $R^5$ are terminal groups composed of an organic group having 1 to 8 carbon atoms and may be the same or different; and at least one of $R^1$ and $R^5$ is a chain organic group having 1 to 8 carbon atoms wherein one or more hydrogen atoms of the chain organic group is substituted with a group having an amide bond.

In the fluorine-containing ether compound of the present embodiment represented by the above formula (1), $R^1$ and $R^5$ are bonded to an atom other than the carbon atom of $R^2$ or $R^4$. $R^1$ and $R^5$ are terminal groups composed of an organic group having 1 to 8 carbon atoms, and may be the same or different. The organic group forming the terminal group may contain an oxygen atom, a sulfur atom, a nitrogen atom, or the like.

At least one of $R^1$ and $R^5$ is a chain organic group having 1 to 8 carbon atoms wherein one or more hydrogen atoms of the chain organic group are substituted with a group having an amide bond (—NHC(=O)—) (hereinafter, the group may be referred to as "an amide bond-containing organic group"). The direction of the amide bond may be —NH—(C=O)— or —(C=O)—NH—.

In the fluorine-containing ether compound of this embodiment, the amide bond in $R^1$ and/or $R^5$ and the polar group in $R^2$ and $R^4$ have good interaction with the protective layer in the lubricant layer containing the fluorine-containing ether compound.

In an amide bond-containing organic group, the carbon forming the amide bond is difficult to rotate freely. Therefore, the interaction (affinity) of the amide bond in the fluorine-containing ether compound molecule is relatively low. Therefore, it is presumed that each of the amide bond-containing organic group of at least one of $R^1$ and $R^5$ and the polar group (for example, a hydroxy group) of $R^2$ and $R^4$ independently interacts with a large number of functional groups on the surface of the protective layer, and as a result, affinity with the protective layer increases.

In contrast, for example, regarding a conventional fluorine-containing ether compound having an organic group substituted with a hydroxy group instead of the amide bond-containing organic group in the present embodiment, affinity with the protective layer is weak, as compared with the fluorine-containing ether compound of the present embodiment. It is presumed that this is because the degree of freedom of rotation of the hydroxy group is higher than that of the amide bond, and the organic group substituted with the hydroxy group and the polar group (for example, hydroxy group) of $R^2$ and/or $R^4$ are likely to interact with each other.

For example, when the amide bond-containing organic group is a cyclic organic group having 1 to 8 carbon atoms (for example, $CH_3—C(=O)—NH—C_6H_4—$), the amide bond-containing organic group is bulky. For this reason, it becomes difficult for the amide bond-containing organic group and the polar group of $R^2$ and $R^4$ to act independently on the surface of the protective layer. Therefore, in the lubricant layer containing the fluorine-containing ether compound, sufficient affinity between the amide bond and the protective layer cannot be obtained.

Further, when the amide bond-containing organic group is not a chain organic group having 1 to 8 carbon atoms but a cyclic organic group having 1 to 8 carbon atoms, the amide bond-containing organic group becomes bulky. When a thin lubricant layer is formed using such a fluorine-containing ether compound, the coverage is insufficient and the chemical resistance and wear resistance cannot be sufficiently obtained.

In the fluorine-containing ether compound of the present embodiment, the type of the amide bond-containing organic group can be appropriately selected according to the performance required for the lubricant containing the fluorine-containing ether compound. The number of amide bonds (—NHC(=O)—) of the amide bond-containing organic group that is at least one of $R^1$ and $R^5$ is not particularly limited, and may be one, or may be two or more. It is preferable that the number of the amide bonds is one because it is possible to prevent the polarity of the fluorine-containing ether compound from becoming too high and causing pickup, in which the fluorine-containing ether compound adheres to the magnetic head as foreign substance (smear).

The number of carbon atoms of the chain organic group, in which one or more hydrogen atoms of the chain organic group is substituted with a group having an amide bond (—NHC(=O)—) (amide bond-containing organic group), is 1-8. When the number of carbon atoms is 1 to 8, the affinity between the lubricant layer containing the fluorine-containing ether compound and the protective layer is further improved. The chain organic group having 1 to 8 carbon atoms is preferably an alkyl group having 1 to 4 carbon atoms, and more preferably an alkyl group having 1 or 2 carbon atoms. When the chain organic group having 1 to 8 carbon atoms is an alkyl group having 1 to 4 carbon atoms, steric hindrance in the fluorine-containing ether compound can be suppressed, so that the amide bond in the lubricant layer containing the fluorine-containing ether compound has better affinity with the protective layer The chain organic group having 1 to 8 carbon atoms is a chain and may have a branch. The chain organic group having 1 to 8 carbon atoms is preferably a straight chain having no branching in order to suppress steric hindrance in the fluorine-containing ether compound.

In the chain organic group, which has 1 to 8 carbon atoms and in which one or more hydrogen atoms of the chain organic group is substituted with a group having an amide bond (—NHC(=O)—) (amide bond-containing organic group), the carbon atom of the chain organic group having 1 to 8 carbon atoms may be bonded to the carbon atom of the amide bond, or may be bonded to the nitrogen atom of the amide bond.

In the amide bond-containing organic group, the bond on the amide bond (—NHC(=O)—) on the side (terminal side) not bonded to the carbon atom of the chain organic group having 1 to 8 carbon atoms is preferably bonded to, for example, a hydrogen atom, a methyl group, an ethyl group, a propyl group, a butyl group, a trifluoromethyl group or the like. The bond is more preferably bonded to a hydrogen atom or a methyl group.

Specific examples of the chain organic group, which has 1 to 8 carbon atoms and in which one or more hydrogen atoms of the chain organic group is substituted with a group having an amide bond (—NHC(=O)—), include an amide bond-containing organic group represented by the following formula (6) or the following formula (7). Among these amide bond-containing organic groups, the amide bond-containing organic group represented by the formula (6) is particularly preferable from the viewpoint of showing good affinity with the protective layer of the magnetic recording medium.

—CH$_2$CH$_2$C(=O)NH$_2$ (6)

—CH$_2$CH$_2$NHC(=O)CH$_3$ (7)

When only one terminal group of $R^1$ and $R^5$ (for example, $R^5$) is an amide bond-containing organic group, the other terminal group (for example, R) that is not an amide bond-containing organic group can be any group and is not particularly limited. The other terminal group is preferably an organic group having at least one double bond or triple bond, and examples thereof include a group containing an aromatic ring, a group containing a heterocyclic ring, a group containing an alkenyl group, and a group containing an alkynyl group. Alternatively, the other terminal group is preferably an alkyl group having 1 to 8 carbon atoms and the alkyl group may have a substituent.

Specifically, the other terminal group may be a phenyl group, a methoxyphenyl group, a fluorinated phenyl group, a naphthyl group, a phenethyl group, a methoxyphenethyl group, a fluorinated phenethyl group, a benzyl group, a methoxybenzyl group, a naphthylmethyl group, a methoxynaphthyl group, a pyrrolyl group, a pyrazolyl group, a methylpyrazolylmethyl group, an imidazolyl group, a furyl group, a furfuryl group, an oxazolyl group, an isoxazolyl group, a thienyl group, a thienylethyl group, a thiazolyl group, a methylthiazolylethyl group, an isothiazolyl group, a pyridyl group, a pyrimidinyl group, a pyridazinyl group, a pyrazinyl group, an indolinyl group, a benzofuranyl group, a benzothienyl group, a benzoimidazolyl group, a benzoxazolyl group, a benzothiazolyl group, a benzopyrazolyl group, a benzoisoxazolyl group, a benzoisothiazolyl group, a quinolyl group, an isoquinolyl group, a quinazolinyl group, a quinoxalinyl group, a phthalazinyl group, a cinnolinyl group, a vinyl group, an allyl group, a butenyl group, a propynyl group, a propargyl group, a butynyl group, a methylbutynyl group, a pentynyl group, a methylpentynyl group, a hexynyl group, a nitrile ethyl group, a methyl group, an ethyl group, a propyl group, a butyl group, a pentyl group, a hexyl group, an octyl, a trifluoromethyl group, a perfluoroethyl group, a perfluoropropyl group, a perfluorobutyl group, a perfluoropentyl group, a perfluorohexyl group, an octafluoropentyl group, or a tridecafluorooctyl group.

Among the above groups, it is preferable that the other terminal group is a phenyl group, a methoxyphenyl group, a thienylethyl group, a butenyl group, an allyl group, a propargyl group, a phenethyl group, a methoxyphenethyl group, or a fluorinated phenethyl group. It is more preferable that the other terminal group is a phenyl group, a thienylethyl group, or an allyl group. In this case, the obtained fluorine-containing ether compound can form a lubricant layer having better wear resistance.

The other terminal group may have a substituent such as an alkyl group, an alkoxy group, a hydroxy group, a mercapto group, a carboxy group, a carbonyl group, or an amino group.

When only one terminal group (for example, $R^1$) of $R^1$ and $R^5$ is an amide bond-containing organic group, the other terminal group (for example, $R^5$) that is not an amide bond-containing organic group may be an organic group having 1 to 8 carbon atoms, which has at least one polar group. It is preferable that the organic group is an alkyl group in which one or more hydrogens are substituted with a polar group. In this case, the affinity between the lubricant layer containing the fluorine-containing ether compound and the protective layer is further improved.

When one terminal group (for example, $R^1$) is an amide bond-containing organic group and the other terminal group (for example, $R^5$) is an organic group having 1 to 8 carbon atoms having at least one polar group, examples of the polar group of the other terminal group include a hydroxy group (—OH) and a cyano group (—CN), and a hydroxy group is preferable.

The organic group having 1 to 8 carbon atoms having at least one polar group is preferably a group represented by the following formula (21). The group represented by the formula (21) is an alkyl group having 1 to 6 carbon atoms in which one hydrogen atom arranged at the terminal is substituted with a hydroxy group. When the organic group is a group represented by the formula (21), the affinity between the lubricant layer containing the fluorine-containing ether compound and the protective layer is further improved, which is preferable.

[Chemical Formula 1]

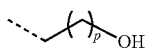
(21)

In formula (21), p represents an integer of 0 to 5.

In the formula (21), p represents an integer of 0 to 5, and preferably p represents an integer of 0 to 2. That is, the organic group is preferably any one selected from a hydroxymethyl group, a hydroxyethyl group, and a hydroxypropyl group. It is preferable that p is 5 or less because the surface free energy of the whole molecule does not become too low due to the low proportion of fluorine atoms in the molecule.

$R^2$ and $R^4$ in the formula (1) are divalent linkage groups having a polar group. $R^2$ and $R^4$ may be the same or different. Since $R^2$ and $R^4$ in the formula (1) have a polar group, when the lubricant layer is formed on the protective layer using the lubricant containing the fluorine-containing ether compound of this embodiment, a suitable interaction between the lubricant layer and the protective layer occurs. The divalent linkage group having a polar group can be appropriately selected according to the performance required for the lubricant containing the fluorine-containing ether compound.

Examples of the polar group of the divalent linkage group having a polar group include a hydroxy group (—OH), an amino group (—NH$_2$), a carboxy group (—COOH), a formyl group (—COH), a carbonyl group (—CO—), a sulfonic acid group (—SO$_3$H) and the like. Of these, the polar group is particularly preferably a hydroxy group. The hydroxy group has a large interaction with a protective layer, particularly a protective layer formed of a carbon-based material. Therefore, when the polar group is a hydroxy group, the lubricant layer containing the fluorine-containing ether compound has high adhesion to the protective layer.

$R^2$ and $R^4$ in the formula (1) are preferably the following formula (2-1).

—(O—CH$_2$CH(OH)CH$_2$)$_a$—O— (2-1)

In the formula (2-1), a represents an integer of 1 to 3.

When in the formula (2-1), a is one or more, the interaction between the polar group of $R^2$ and $R^4$ and the protective layer becomes even stronger. As a result, by using the fluorine-containing ether compound, it is possible to obtain a lubricant layer having higher adhesion to the protective layer. Further, when the above a is 3 or less, it is possible to prevent pickup, in which the fluorine-containing ether compound adheres to the magnetic head as a foreign substance (smear) due to high polarity of the fluorine-containing ether compound.

In the fluorine-containing ether compound represented by the formula (1), when $R^2$ and $R^4$ are represented by the above formula (2-1), a chain-bonded carbon atom and oxygen atom (at least —O—CH$_2$—) are arranged between the amide bond of $R^1$ and/or $R^5$ and the carbon atom to which the polar group of $R^2$ and $R^4$ is bonded. Therefore, for example, as compared with the case where the amide bond of $R^1$ and/or $R^5$ and the polar group of $R^2$ and $R^4$ are bonded to the same carbon (—C(polar group)-NHC(=O)— or —C(polar group)-C(=O)NH—), the interaction between the amide bond and the polar group is weak. On the other hand, the interaction between both the amide bond and the polar group and a large number of functional groups present on the surface of the protective layer is relatively strong compared to the case where the amide bond and the polar group are bonded to the same carbon. As a result, the affinity between the lubricant layer and the protective layer increases when the lubricant layer is formed on the protective layer using the lubricant containing the fluorine-containing ether compound.

Therefore, when $R^2$ and $R^4$ are represented by the above formula (2-1), the lubricant layer formed using the lubricant containing the fluorine-containing ether compound has better chemical resistance and wear resistance. From the viewpoint of the affinity between the lubricant layer and the protective layer, the total number of chain-bonded carbon atoms and oxygen atoms present between the carbon of $R^1$ and/or $R^5$ to which the amide bond is bonded and the carbon of $R^2$ and/or $R^4$ to which the polar group on the most terminal side is bonded is preferably 2 to 5.

$R^3$ in the formula (1) is a perfluoropolyether chain (hereinafter sometimes referred to as "PFPE chain"). In the lubricant layer containing the fluorine-containing ether compound of this embodiment, the PFPE chain covers the surface of the protective layer and reduces the frictional force between the magnetic head and the protective layer. The PFPE chain can be appropriately selected according to the performance required for the lubricant containing the fluorine-containing ether compound.

Examples of the PFPE chain include a perfluoromethylene oxide polymer, a perfluoroethylene oxide polymer, a perfluoro-n-propylene oxide polymer, a perfluoroisopropylene oxide polymer, and a copolymer thereof.

Specifically, $R^3$ in the formula (1) is preferably any one of the following formulas (3) to (5). When $R^3$ is any one of the formulas (3) to (5), a fluorine-containing ether compound which may be used for a lubricant layer having good lubricity can be obtained.

In addition, (CF$_2$CF$_2$O) and (CF$_2$O) which are repeating units in the formula (3) may be bonded in a block manner, or a part or all of them may be bonded at random.

—CF$_2$O—(CF$_2$CF$_2$O)$_c$—(CF$_2$O)$_d$—CF$_2$— (3)

In the formula (3), c and d represent the average degree of polymerization and each represents 0 to 20, and c or d is 0.1 or more.

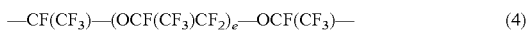

$$—CF(CF_3)—(OCF(CF_3)CF_2)_e—OCF(CF_3)— \quad (4)$$

In the formula (4), e represents the average degree of polymerization and represents 0.1 to 20.

$$—CF_2CF_2—(OCF_2CF_2CF_2)_f—OCF_2CF_2— \quad (5)$$

In the formula (5), f represents the average degree of polymerization and represents 0.1 to 20.

In the formulas (4) to (5), e and f are each 0.1 to 20 (or in the formula (3), c and d are each 0 to 20 and c or d is 0.1 or more). Thus, a fluorine-containing ether compound which may be used to produce a lubricant layer having good lubricity can be obtained. However, when c, d, e, and f exceed 20, the viscosity of the fluorine-containing ether compound increases, and it may be difficult to apply a lubricant containing the compound. Therefore, c, d, e, and f are preferably 20 or less.

In the fluorine-containing ether compound represented by the formula (1), $R^1$ and R may be the same or different. $R^1$ and $R^5$ are preferably the same in view of ease of production.

In the fluorine-containing ether compound represented by the formula (1), $R^2$ and $R^4$ may be the same or different. $R^2$ and $R^4$ are preferably the same in view of ease of production.

Therefore, in the fluorine-containing ether compound represented by the formula (1), it is preferable that $R^1$ and $R^5$ are the same and that $R^2$ and $R^4$ are the same in view of ease of production.

Specifically, the fluorine-containing ether compound represented by the formula (1) is preferably any one of compounds represented by the following formulas (A) to (M). Note that the repetition numbers m and n in the formulas (A) to (M) are values indicating average values, and are not necessarily integers.

In the compounds represented by the formula (A), $R^1$ and $R^5$ are each an amide bond-containing organic group represented by the formula (6); $R^2$ and $R^4$ are each represented by the formula (2-1); $R^1$ and $R^5$ are the same and $R^2$ and $R^4$ are the same; and $R^3$ is represented by the formula (3).

In the compound represented by the formula (B), $R^1$ and $R^5$ are each an amide bond-containing organic group represented by the formula (7); $R^2$ and $R^4$ are each represented by the formula (2-1); $R^1$ and $R^5$ are the same, and $R^2$ and $R^4$ are the same; and $R^3$ is represented by the formula (3).

In the compounds represented by the formulas (C) to (E) and (G) to (I), $R^1$ and $R^5$ are different, $R^5$ is an amide bond-containing organic group represented by the formula (6) or the formula (7), and $R^1$ is one of a phenyl group, a thienylethyl group, and an allyl group; $R^2$ and $R^4$ are the same, $R^2$ and $R^4$ are each represented by the formula (2-1); and $R^3$ is represented by the formula (3).

In the compounds represented by the formulas (F) and (J), R and $R^5$ are different, $R^5$ is an amide bond-containing organic group represented by the formula (6) or the formula (7), and $R^1$ is an allyl group; $R^2$ is the formula (2-1) in which a is 2, $R^4$ is represented by formula (2-1) in which a is 1; and $R^3$ is represented by formula (3).

In the compound represented by the formula (K), $R^1$ and $R^5$ are different, $R^5$ is an amide bond-containing organic group represented by the formula (7), and $R^1$ is an allyl group; $R^2$ and $R^4$ are the same, $R^2$ and $R^4$ are each represented by the formula (2-1); and $R^3$ is represented by the formula (5).

In the compound represented by the formula (L), $R^1$ and $R^5$ are different, $R^5$ is an amide bond-containing organic group represented by the formula (7), and $R^1$ is a group represented by the formula (21) in which p is 1; $R^2$ and $R^4$ are the same, $R^2$ and $R^4$ are each represented by the formula (2-1); and $R^3$ is represented by the formula (3).

In the compound represented by the formula (M), $R^1$ and $R^5$ are different, $R^5$ is an amide bond-containing organic group represented by the formula (7), and $R^1$ is a group represented by the formula (21) in which p is 1; $R^2$ and $R^4$ are the same, $R^2$ and $R^4$ are represented by the formula (2-1) in which a=2; and $R^3$ is represented by the formula (3).

[Chemical Formula 2]

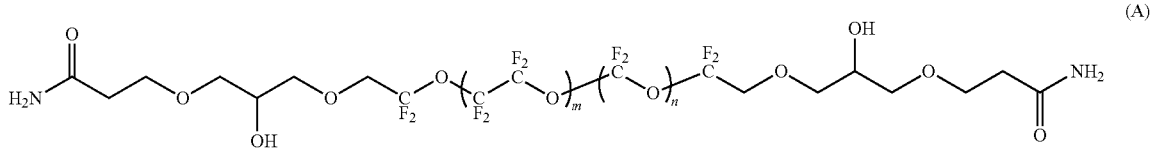

(A)

In the formula (A), m and n represent the average degree of polymerization and are each 0.1 to 20.

[Chemical Formula 3]

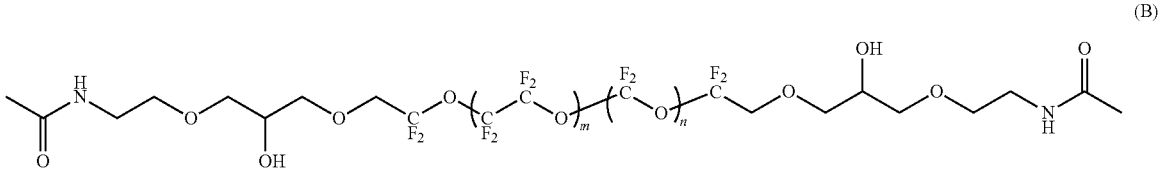

(B)

In the formula (B), m and n represent the average degree of polymerization and are each 0.1 to 20.

[Chemical Formula 4]

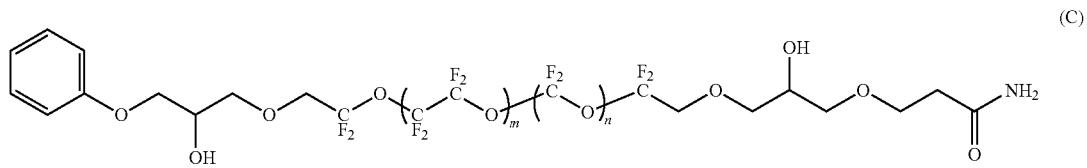

(C)

In the formula (C), m and n represent the average degree of polymerization and are each 0.1 to 20.

[Chemical Formula 5]

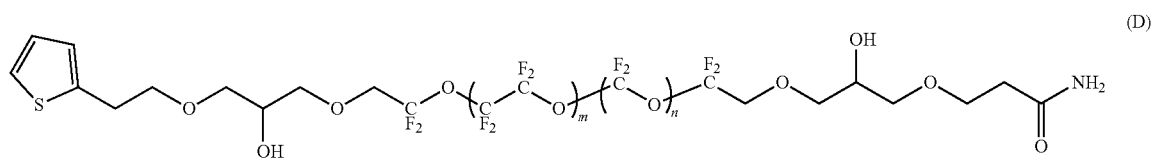

(D)

In the formula (D), m and n represent the average degree of polymerization and are each 0.1 to 20.

[Chemical Formula 6]

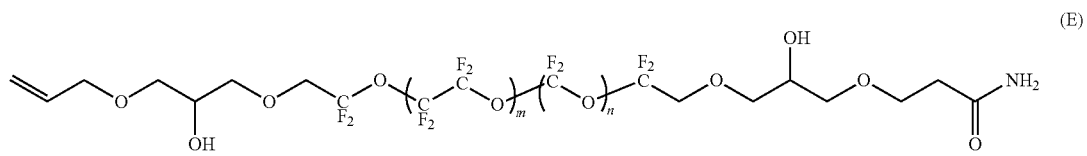

(E)

In the formula (E), m and n represent the average degree of polymerization and are each 0.1 to 20.

[Chemical Formula 7]

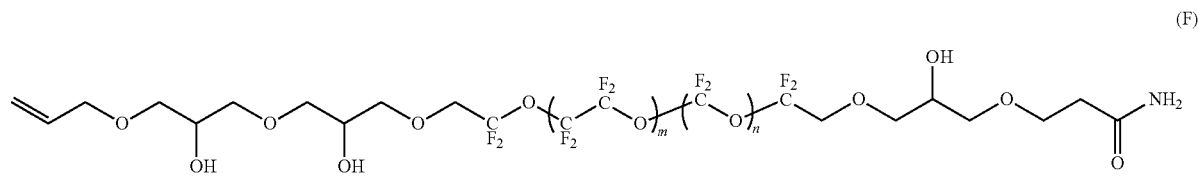

(F)

In the formula (F), m and n represent the average degree of polymerization and are each 0.1 to 20.

[Chemical Formula 8]

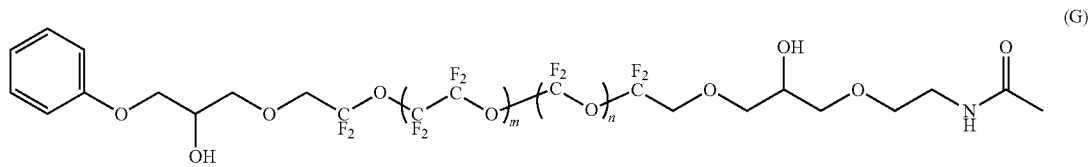

(G)

In the formula (G), m and n represent the average degree of polymerization and are each 0.1 to 20.

In the formula (L), m and n represent the average degree of polymerization and are each 0.1 to 20.

[Chemical Formula 9]

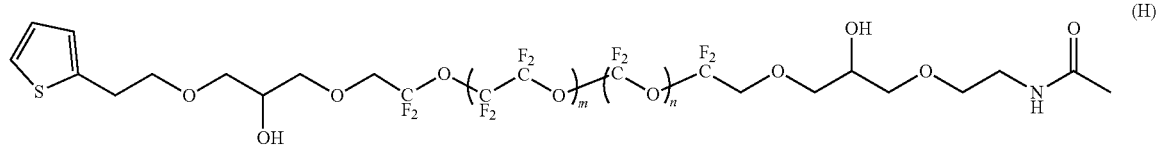
(H)

In the formula (H), m and n represent the average degree of polymerization and are each 0.1 to 20.

In the formula (M), m and n represent the average degree of polymerization and are each 0.1 to 20.

[Chemical Formula 10]

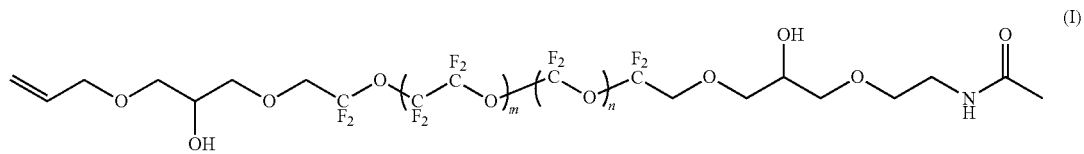
(I)

In the formula (I), m and n represent the average degree of polymerization and are each 0.1 to 20.

The number average molecular weight (Mn) of the fluorine-containing ether compound represented by the formula

[Chemical Formula 11]

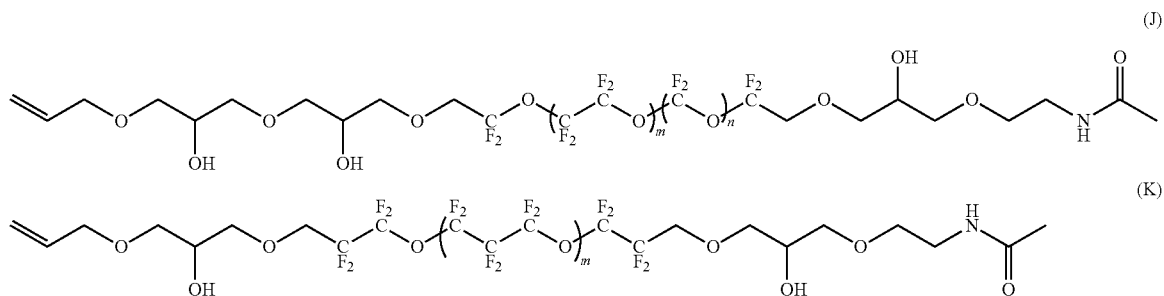
(J)

(K)

In the formula (J), m and n represent the average degree of polymerization and are each 0.1 to 20.

In the formula (K), m represents the average degree of polymerization and is 1 to 20.

(1) is preferably in the range of 500 to 10,000, particularly preferably 1,000 to 5,000. When the number average molecular weight is 500 or more, the lubricant layer containing the fluorine-containing ether compound of the pres-

[Chemical Formula 7]

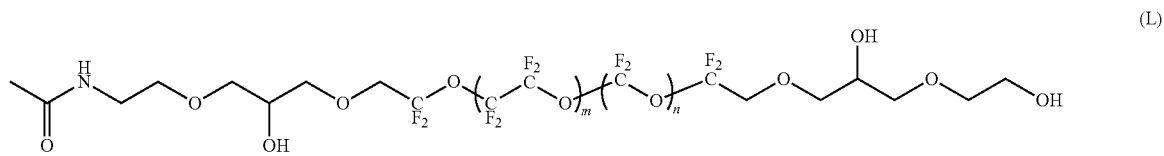
(L)

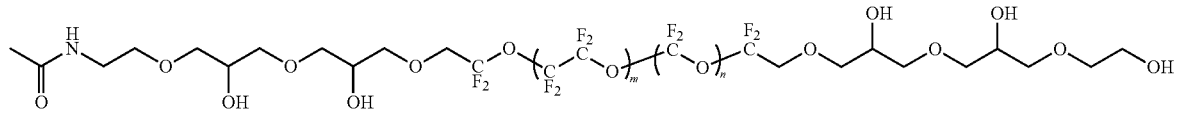
(M)

ent embodiment has excellent heat resistance. The number average molecular weight of the fluorine-containing ether compound is more preferably 1000 or more. Further, when the number average molecular weight is 10,000 or less, the viscosity of the fluorine-containing ether compound becomes appropriate, and a thin lubricant layer can be easily formed by applying a lubricant containing the fluorine-containing ether compound. The number average molecular weight of the fluorine-containing ether compound is preferably 5000 or less because the viscosity of the lubricant using the fluorine-containing ether compound becomes easy to handle.

The number average molecular weight (Mn) of the fluorine-containing ether compound is a value measured by $^1$H-NMR and $^{19}$F-NMR by using AVANCE 111-400 manufactured by Bruker BioSpin. Specifically, the number of repeating units of the PFPE chain are calculated from the integral value measured by $^{19}$F-NMR, and then the number average molecular weight are calculated. In NMR (nuclear magnetic resonance) measurement, a sample was diluted in d-acetone or hexafluorobenzene/d-acetone (¼ (v/v)) solvent and used for measurement. The standard for $^{19}$F-NMR chemical shift was set to −164.7 ppm for the hexafluorobenzene peak, and the standard for H-NMR chemical shift was set to 2.2 ppm for acetone.

The fluorine-containing ether compound represented by the formula (1) preferably has a molecular weight dispersity (ratio (Mw/Mn) of weight average molecular weight (Mw) and number average molecular weight (Mn)) of 1.3 or less, by carrying out molecular weight fractionation.

The method of carrying out molecular weight fractionation need not be particularly limited. For example, molecular weight fractionation may be carried out by silica gel column chromatography method, gel permeation chromatography (GPC) method, or the like. Molecular weight fractionation may also be carried out by supercritical extraction method.

"Production Method"

The method for producing the fluorine-containing ether compound of the present embodiment is not particularly limited, and the fluorine-containing ether compound can be produced using a conventionally known production method. The fluorine-containing ether compound of this embodiment can be produced using the method shown below, for example.

For example, a method of reacting a perfluoropolyether compound, having a perfluoropolyether main chain in the molecule and having hydroxy groups at both terminals, with a compound including an epoxy group at one terminal and an amide bond-containing organic group at the other terminal, may be used. Examples of the compound having an epoxy group at one terminal and an amide bond-containing organic group at the other terminal include the compounds represented by the following formulas (8) to (11).

[Chemical Formula 13]

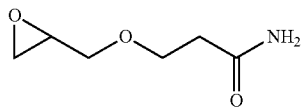

(8)

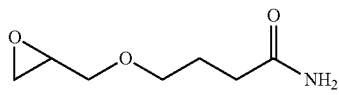

(9)

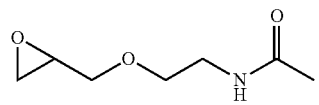

(10)

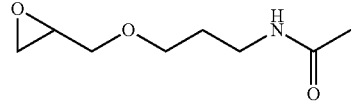

(11)

In the fluorine-containing ether compound of the present embodiment, as shown in the above formula (1), a divalent linkage group having a polar group represented by $R^2$ and $R^4$ is linked to both terminals of the PFPE chain represented by $R^3$. An amide bond-substituted organic group is bonded to at least one of them ($R^1$ and/or R).

In the lubricant layer containing the fluorine-containing ether compound of this embodiment, the PFPE chain covers the surface of the protective layer and reduces the frictional force between the magnetic head and the protective layer. It is possible to improve affinity between the lubricant layer containing the fluorine-containing ether compound of the present embodiment and the protective layer by combination of the $R^2$ and $R^4$ arranged at both terminals of the PFPE chain and an amide bond-containing organic group bonded to at least one of them. As a result, when the lubricant layer is formed on the protective layer of the magnetic recording medium using the lubricant containing the fluorine-containing ether compound of the present embodiment, a lubricant layer in which high coverage rate can be obtained even if the film thickness is small and which has excellent chemical resistance and wear resistance can be formed.

[Lubricant for Magnetic Recording Media]

The lubricant for magnetic recording medium of this embodiment contains a fluorine-containing ether compound represented by the formula (1).

The lubricant of the present embodiment may use one or more known materials used as a lubricant material by mixing them as necessary, as long as the known material does not impair the characteristics obtained by containing the fluorine-containing ether compound represented by the formula (1).

Specific examples of known materials include, for example, FOMBLIN (registered trademark) ZDIAC, FOBLIN ZDEAL, FOMBLIN AM-2001 (the above materials are manufactured by Solvay Solexis), Moresco A20H (manufactured by Moresco) and the like. The known material used in combination with the lubricant of this embodiment preferably has a number average molecular weight of 1000 to 10,000.

When the lubricant of this embodiment contains materials other than the fluorine-containing ether compound represented by formula (1), the amount of the fluorine-containing ether compound represented by formula (1) in the lubricant of this embodiment is preferably 50% by mass or more, and more preferably 70% by mass or more.

Since the lubricant of this embodiment contains the fluorine-containing ether compound represented by the formula (1), the surface of the protective layer can be coated with a high coverage rate even when the thickness is reduced. As a result, a lubricant layer having excellent chemical resistance and wear resistance can be formed.

[Magnetic Recording Medium]

The magnetic recording medium of the present embodiment is obtained by providing at least a magnetic layer, a protective layer, and a lubricant layer sequentially on a substrate.

In the magnetic recording medium of the present embodiment, one or more base layers can be provided between the substrate and the magnetic layer as necessary. Further, an adhesion layer and/or a soft magnetic layer can be provided between the base layer and the substrate.

FIG. 1 is a schematic cross-sectional view showing an embodiment of the magnetic recording medium of the present invention.

The magnetic recording medium 10 of this embodiment has a structure in which an adhesion layer 12, a soft magnetic layer 13, a first base layer 14, a second base layer 15, a magnetic layer 16, a protective layer 17 and a lubricant layer 18 are sequentially provided on a substrate 11.

"Substrate"

As the substrate 11, for example, a nonmagnetic substrate in which a film made of NiP or NiP alloy is formed on a base made of a metal or alloy material such as Al or Al alloy can be used.

The substrate 11 may use a nonmagnetic substrate made of a nonmetallic material such as glass, ceramics, silicon, silicon carbide, carbon, or resin; or may use a nonmagnetic substrate obtained by forming a film made of NiP or NiP alloy on a base made of these nonmetallic materials.

The glass substrate is suitable for increasing the recording density because it has rigidity and excellent smoothness. Examples of the glass substrates include an aluminosilicate glass substrate, and a chemically strengthened aluminosilicate glass substrate, which is particularly preferable.

The roughness of the main surface of the substrate 11 is preferably ultra-smooth with Rmax of 6 nm or less and Ra of 0.6 nm or less. Here, the surface roughness Rmax and Ra are based on the standards of JIS B0601.

"Adhesion Layer"

The adhesion layer 12 prevents the progress of corrosion of the substrate 11 that occurs when the substrate 11 and the soft magnetic layer 13 provided on the adhesion layer 12 are disposed in contact with each other.

The material of the adhesion layer 12 may be appropriately selected from, for example, Cr, Cr alloy, Ti, Ti alloy, CrTi, NiAl, AIRu alloy and the like. The adhesion layer 12 can be formed by, for example, a sputtering method.

"Soft Magnetic Layer"

The soft magnetic layer 13 preferably has a structure in which a first soft magnetic film, an intermediate layer made of a Ru film, and a second soft magnetic film are sequentially stacked. That is, it is preferable that the soft magnetic layer 13 has a structure in which the soft magnetic films above and below the intermediate layer are linked by antiferromagnetic coupling (AFC) by sandwiching the intermediate layer made of a Ru film between the two soft magnetic films.

Examples of the material of the first soft magnetic film and the second soft magnetic film include a CoZrTa alloy and a CoFe alloy.

It is preferable to add any one of Zr, Ta, and Nb to the CoFe alloy used for the first soft magnetic film and the second soft magnetic film. This promotes the amorphization of the first soft magnetic film and the second soft magnetic film, and as a result, it becomes possible to improve the orientation of the first base layer (seed layer) and reduce the floating height of the magnetic head.

The soft magnetic layer 13 can be formed by, for example, a sputtering method.

"First Base Layer"

The first base layer 14 is a layer for controlling the orientation and crystal size of the second base layer 15 and the magnetic layer 16 provided on top of the first base layer 14.

Examples of the first base layer 14 include a Cr layer, a Ta layer, a Ru layer, a CrMo alloy layer, a CoW alloy layer, a CrW alloy layer, a CrV alloy layer, and a CrTi alloy layer.

The first base layer 14 can be formed by, for example, a sputtering method.

"Second Base Layer"

The second base layer 15 is a layer for turning the magnetic layer 16 to a more favorable orientation. The second base layer 15 is preferably a layer made of Ru or a Ru alloy.

The second base layer 15 may be composed of a single layer or may be composed of a plurality of layers. When the second base layer 15 is composed of a plurality of layers, all the layers may be formed from the same material, or at least one layer may be formed from a different material.

The second base layer 15 can be formed by, for example, a sputtering method.

"Magnetic Layer"

The magnetic layer 16 is made of a magnetic film whose easy magnetization axis is oriented perpendicularly or horizontally to the substrate surface. The magnetic layer 16 is a layer containing Co and Pt, and may be a layer containing an oxide, Cr, B, Cu, Ta, Zr or the like in order to further improve the SNR characteristics.

Examples of the oxide contained in the magnetic layer 16 include $SiO_2$, SiO, $Cr_2O_3$, CoO, $Ta_2O_3$, and $TiO_2$.

The magnetic layer 16 may be composed of one layer, or may be composed of a plurality of magnetic layers made of materials having different compositions.

For example, when the magnetic layer 16 is composed of three layers of a first magnetic layer, a second magnetic layer, and a third magnetic layer that are stacked in order from the bottom, it is preferable that the first magnetic layer has a granular structure that includes a material containing Co, Cr, and Pt and further containing an oxide. As the oxide contained in the first magnetic layer, for example, an oxide of each Cr, Si, Ta, Al, Ti, Mg, and Co is preferably used. Among these, $TiO_2$, $Cr_2O_3$, $SiO_2$ or the like can be preferably used. The first magnetic layer is preferably made of a composite oxide in which two or more types of oxides are added. Of these, $Cr_2O_3$—$SiO_2$, $Cr_2O_3$—$TiO_2$, $SiO_2$—$TiO_2$ or the like can be preferably used.

The first magnetic layer may include at least one element selected from B, Ta, Mo, Cu, Nd, W, Nb, Sm, Tb, Ru, and Re in addition to Co, Cr, Pt, and oxide.

The same material as those used for the first magnetic layer can be used for the second magnetic layer. The second magnetic layer preferably has a granular structure.

The third magnetic layer preferably has a non-granular structure made of a material containing Co, Cr, Pt but containing no oxide. The third magnetic layer may contain one or more elements selected from B, Ta, Mo, Cu, Nd, W, Nb, Sm, Tb, Ru, Re, and Mn in addition to Co, Cr, and Pt.

When the magnetic layer 16 is formed of a plurality of magnetic layers, it is preferable to provide a nonmagnetic layer between adjacent magnetic layers. When the magnetic layer 16 is composed of three layers of the first magnetic layer, the second magnetic layer, and the third magnetic layer, it is preferable to provide a nonmagnetic layer between the first magnetic layer and the second magnetic layer, and between the second magnetic layer and the third magnetic layer.

Examples of materials that can be used favorably for the non-magnetic layers provided between the adjacent magnetic layers of the magnetic layer 16 include Ru, a Ru alloy, a CoCr alloy, and a CoCrX1 alloy (wherein X1 represents one or more elements selected from among Pt, Ta, Zr, Re, Ru, Cu, Nb, Ni, Mn, Ge, Si, O, N, W, Mo, Ti, V and B) and the like.

It is preferable to use an alloy material containing an oxide, a metal nitride, or a metal carbide for the nonmagnetic layer provided between the adjacent magnetic layers of the magnetic layer 16. Specific examples of oxides that may be used include $SiO_2$, $Al_2O_3$, $Ta_2O$, $Cr_2O_3$, $MgO$, $Y_2O_3$, $TiO_2$, and the like. Examples of metal nitrides that may be used include AlN, $Si_3N_4$, TaN, CrN, and the like. Examples of metal carbides that may be used include TaC, BC, SiC, and the like.

The nonmagnetic layer can be formed by, for example, a sputtering method.

The magnetic layer 16 is preferably a magnetic layer for perpendicular magnetic recording in which the easy magnetization axis is oriented in a direction perpendicular to the substrate surface in order to achieve a higher recording density. The magnetic layer 16 may be in-plane magnetic recording.

The magnetic layer 16 may be formed by using any conventionally known method such as a vapor deposition method, an ion beam sputtering method, or a magnetron sputtering method. The magnetic layer 16 is usually formed by a sputtering method.

"Protective Layer" The protective layer 17 protects the magnetic layer 16. The protective layer 17 may be composed of one layer or may be composed of a plurality of layers. As the protective layer 17, a carbon-based protective layer can be preferably used, and an amorphous carbon protective layer is particularly preferable. It is preferable that the protective layer 17 is a carbon-based protective layer because interaction with a polar group (particularly a hydroxy group) contained in the fluorine-containing ether compound in the lubricant layer 18 is further increased.

The adhesion between the carbon-based protective layer and the lubricant layer 18 can be controlled by making the carbon-based protective layer to contain hydrogenated carbon and/or nitrogenated carbon, and then adjusting the hydrogen content and/or the nitrogen content in the carbon-based protective layer. The hydrogen content in the carbon-based protective layer is preferably 3 to 20 atomic % as measured by the hydrogen forward scattering method (HFS). Further, the nitrogen content in the carbon-based protective layer is preferably 4 to 15 atomic % as measured by X-ray photoelectron spectroscopy (XPS).

The hydrogen and/or nitrogen contained in the carbon-based protective layer need not be uniformly contained in the entire carbon-based protective layer. For example, the carbon-based protective layer is preferably a composition gradient layer in which nitrogen is contained on the lubricant layer 18 side of the protective layer 17 and hydrogen is contained on the magnetic layer 16 side of the protective layer 17. In this case, the adhesion between the magnetic layer 16 and the carbon-based protective layer and the adhesion between the lubricant layer 18 and the carbon-based protective layer are further improved.

The film thickness of the protective layer 17 is preferably 1 nm to 7 nm. When the thickness of the protective layer 17 is 1 nm or more, the performance of the protective layer 17 is sufficiently obtained. The thickness of the protective layer 17 is preferably 7 nm or less from the viewpoint of reducing the thickness of the protective layer 17.

As a method for forming the protective layer 17, a sputtering method using a target material containing carbon, a chemical vapor deposition (CVD) method using a hydrocarbon raw material such as ethylene or toluene, an ion beam deposition (IBD) method, or the like can be used.

When a carbon-based protective layer is formed as the protective layer 17, it can be formed by, for example, a DC magnetron sputtering method. In particular, when a carbon-based protective layer is formed as the protective layer 17, it is preferable to form an amorphous carbon protective layer by plasma CVD. The amorphous carbon protective layer formed by the plasma CVD method has a uniform surface and small roughness.

"Lubricant Layer"

The lubricant layer 18 prevents contamination of the magnetic recording medium 10. Further, the lubricant layer 18 reduces the frictional force of the magnetic head of the magnetic recording/reproducing apparatus that slides on the magnetic recording medium 10, and improves the durability of the magnetic recording medium 10.

The lubricant layer 18 is formed on and is in contact with the protective layer 17, as shown in FIG. 1. The lubricant layer 18 includes the above-described fluorine-containing ether compound.

When the protective layer 17 disposed under the lubricant layer 18 is a carbon-based protective layer, the protective layer 17 is bonded to the fluorine-containing ether compound contained in the lubricant layer 18 with a particularly high bonding strength. As a result, even when the lubricant layer 18 is thin, it is easy to obtain the magnetic recording medium 10 in which the surface of the protective layer 17 is coated with a high coverage rate, and contamination of the surface of the magnetic recording medium 10 can be effectively prevented.

The average film thickness of the lubricant layer 18 is preferably 0.5 nm (5 Å) to 2 nm (20 Å). When the average film thickness of the lubricant layer 18 is 0.5 nm or more, the lubricant layer 18 is formed with a uniform film thickness without forming an island shape or a mesh shape. For this reason, the surface of the protective layer 17 can be covered with the lubricant layer 18 at a high coverage rate. Moreover, by making the average film thickness of the lubricant layer 18 to be 2 nm or less, the lubricant layer 18 can be made sufficiently thin, and the floating height of the magnetic head can be sufficiently reduced.

"Method of Forming Lubricant Layer"

As a method of forming the lubricant layer, for example, a method of preparing a magnetic recording medium in the middle of production in which the layers up to the protective layer 17 are formed on the substrate 11, applying a solution for forming a lubricant layer on the protective layer 17, and then drying the layer, may be used.

The lubricant layer-forming solution can be obtained by dispersing and dissolving the lubricant for magnetic recording medium of the above-described embodiment in a solvent as necessary to obtain a viscosity and concentration suitable for the coating method.

Examples of solvents used in the lubricant layer-forming solution include fluorinated solvents such as Vertrel (registered trademark) XF (trade name, manufactured by Mitsui DuPont Fluorochemical Co., Ltd.).

The method for applying the lubricant layer-forming solution is not particularly limited, and examples thereof include a spin-coating method, a spray method, a paper coating method, and a dip method.

When using the dip method, for example, the following method can be used. First, the substrate 11 on which the layers up to the protective layer 17 are formed is dipped in the lubricant layer-forming solution placed in the dipping tank of the dip coater. Subsequently, the substrate 11 is pulled up from the dipping tank at a predetermined speed. Thus, the lubricant layer-forming solution is applied to the surface of the protective layer 17 on the substrate 11.

By using the dip method, the lubricant layer-forming solution can be applied uniformly to the surface of the protective layer 17, and the lubricant layer 18 can be formed on the protective layer 17 with a uniform film thickness.

In this embodiment, it is preferable to heat the substrate 11 on which the lubricant layer 18 is formed. By performing the heat treatment, the adhesion between the lubricant layer 18 and the protective layer 17 is improved, and the adhesive strength between the lubricant layer 18 and the protective layer 17 is improved.

The heat treatment temperature is preferably 100 to 180° C. When the heat treatment temperature is 100° C. or higher, the effect of improving the adhesion between the lubricant layer 18 and the protective layer 17 is sufficiently obtained. Moreover, thermal decomposition of the lubricant layer 18 can be prevented by setting the heat treatment temperature to 180° C. or lower. The heat treatment time is preferably 10 to 120 minutes.

In this embodiment, in order to further improve the adhesion of the lubricant layer 18 to the protective layer 17, the lubricant layer 18 of the substrate 11 before or after the heat treatment may be subjected to a process of irradiating ultraviolet rays (UV).

The magnetic recording medium 10 of the present embodiment is obtained by sequentially providing at least a magnetic layer 16, a protective layer 17, and a lubricant layer 18 on a substrate 11. In the magnetic recording medium 10 of the present embodiment, the lubricant layer 18 containing the above-mentioned fluorine-containing ether compound is formed on and in contact with the protective layer 17. The lubricant layer 18 has excellent chemical substance resistance and wear resistance even when the thickness is small. Therefore, the magnetic recording medium 10 according to the present embodiment is excellent in reliability, and in particular, is excellent in suppression of silicon contamination and wear resistance. Therefore, the magnetic recording medium 10 of the present embodiment, which has a low magnetic head floating height (for example, 10 nm or less), and which has high reliability that operates stably over a long period of time even in a severe environment due to diversification of applications, can be obtained. For this reason, the magnetic recording medium 10 of this embodiment is particularly suitable as a magnetic disk mounted in a LUL type magnetic disk device.

EXAMPLE

Hereinafter, the present invention will be described more specifically with reference to examples and comparative examples. In addition, this invention is not limited only to the following examples.

Example 1

By the method shown below, the compound represented by the above formula (A) (In the formula (A), m indicating the average degree of polymerization is 4.5 and n indicating the average degree of polymerization is 4.5) was obtained. Hereinafter, the compound represented by the formula (A) is referred to as Compound (A).

First, 3-hydroxypropamide and allyl bromide were reacted in tetrahydrofuran in the presence of a base to obtain a compound. Subsequently, the obtained compound was oxidized in dichloromethane using metachloroperbenzoic acid to synthesize a compound represented by the above formula (8).

Next, in a 200 mL eggplant flask under a nitrogen atmosphere, 20 g of a fluoropolyether (number average molecular weight 1000, molecular weight distribution 1.1) represented by $HOCH_2CF_2O(CF_2CF_2O)_h(CF_2O)_iCF_2CH_2OH$ (wherein h indicating an average polymerization degree is 4.5 and i indicating an average polymerization degree is 4.5), 6.38 g of a compound represented by the above formula (8), and 20 mL of t-butanol were charged and stirred at room temperature until uniform.

To this homogeneous solution, 0.90 g of potassium tert-butoxide was added and stirred at 70° C. for 14 hours for reaction. The obtained reaction product was cooled to 25° C., neutralized with 1 mol/L hydrochloric acid, extracted with Vertrel XF (hereinafter sometimes abbreviated as "Vertrel XF") manufactured by Mitsui DuPont Fluorochemical, and washed with water. The organic layer was dehydrated with anhydrous sodium sulfate. After the desiccant was filtered off, the filtrate was concentrated. The residue was purified by silica gel column chromatography to obtain Compound (A).

$^1$H-NMR measurement of the obtained Compound (A) was performed, and the structure was identified from the following results.

$^1$H-NMR (acetone-$D_6$): δ [ppm]=2.20-2.30 (4H), 3.60-4.30 (18H), 7.00-7.10 (4H)

Example 2

By the method shown below, the compound represented by the above formula (B) (in the formula (B), m indicating the average degree of polymerization is 4.5 and n indicating the average degree of polymerization is 4.5) was obtained. Hereinafter, the compound represented by the formula (B) is referred to as Compound (B).

A compound represented by the above formula (10) was synthesized in the same manner as Compound (8) except that 2-acetamidoethanol was used instead of 3-hydroxypropamide.

Then, Compound (B) was obtained in the same manner as in Example 1, except that 7.00 g of the compound represented by the above formula (10) was used instead of the compound represented by the above formula (8) in Example 1.

$^1$H-NMR measurement of the obtained Compound (B) was performed, and the structure was identified by the following results.

$^1$H-NMR (acetone-$D_6$): δ [ppm]=2.00 (6H), 3.35-3.45 (4H), 3.60-4.20 (18H), 7.50 (2H)

Example 3

By the method shown below, the compound represented by the above formula (C) (in formula (C), m indicating the average degree of polymerization is 4.5 and n indicating the average degree of polymerization is 4.5) was obtained. Hereinafter, the compound represented by the formula (C) is referred to as Compound (C).

In a 200 mL eggplant flask under a nitrogen atmosphere, 20 g of a fluoropolyether (number average molecular weight 1000, molecular weight distribution 1.1) represented by $HOCH_2CF_2O(CF_2CF_2O)_h(CF_2O)_iCF_2CH_2OH$ (wherein h indicating an average degree of polymerization is 4.5 and i indicating an average degree of polymerization is 4.5), 1.50 g of glycidyl phenyl ether, and 10 mL of t-butanol were charged and stirred at room temperature until uniform.

To this homogeneous solution, 0.90 g of potassium tert-butoxide was added, and the mixture was reacted at 70° C. for 8 hours. The obtained reaction product was cooled to 25° C., neutralized with 0.5 mol/L hydrochloric acid, and then extracted with Vertrel XF. The organic layer was washed with water and dehydrated with anhydrous sodium sulfate. After the desiccant was filtered off, the filtrate was concentrated, and the residue was purified by silica gel column chromatography to obtain 7.25 g of a compound represented by the following formula (12) as an intermediate.

[Chemical Formula 14]

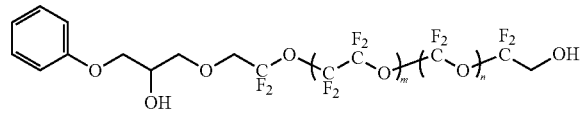

(12)

In the formula (12), m indicating the average degree of polymerization is 4.5, and n indicating the average degree of polymerization is 4.5.

In a 200 mL eggplant flask under a nitrogen gas atmosphere, 7.10 g of the compound represented by the above formula (12), 0.870 g of the compound represented by the above formula (8), and 50 mL of t-butanol were charged and stirred at room temperature until uniform.

To this homogeneous solution, 0.187 g of potassium tert-butoxide was added, and the mixture was reacted at 70° C. for 16 hours. The obtained reaction product was cooled to 25° C., neutralized with 0.1 mol/L hydrochloric acid, and extracted with Vertrel XF. The organic layer was washed with water and dehydrated with anhydrous sodium sulfate. After the desiccant was filtered off the filtrate was concentrated. The residue was purified by silica gel column chromatography to obtain 4.59 g of Compound (C).

$^1$H-NMR measurement of the obtained Compound (C) was performed, and the structure was identified by the following results.

$^1$H-NMR ($CD_3COCD_3$); δ [ppm]=2.20-2.30 (2H), 3.60-4.20 (16H), 6.90 (5H), 7.20 (2H)

Example 4

By the method shown below, the compound represented by the above formula (D) (in formula (D), m indicating the average degree of polymerization is 4.5 and n indicating the average degree of polymerization is 4.5) was obtained. Hereinafter, the compound represented by the above formula (D) is referred to as Compound (D).

An epoxy compound represented by the following formula (13) was synthesized by reacting thiophene ethanol with epibromohydrin. Then, 4.95 g of Compound (D) was obtained in the same manner as in Example 3, except that an epoxy compound represented by the formula (13) was used instead of glycidyl phenyl ether in Example 3 to synthesize a compound represented by the following formula (14) as an intermediate.

[Chemcial Formula 15]

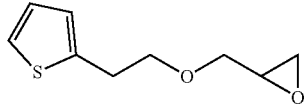

(13)

[Chemcial Formula 16]

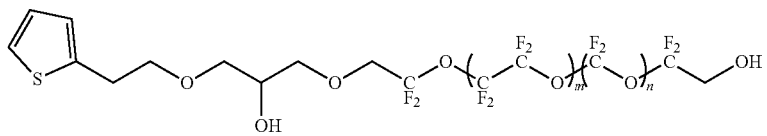

(14)

In formula (14), m indicating the average degree of polymerization is 4.5, and n indicating the average degree of polymerization is 4.5.

$^1$H-NMR measurement of the obtained compound (D) was performed, and the structure was identified by the following results.

$^1$H-NMR ($CD_3COCD_3$): δ[ppm]=2.20-2.30 (2H), 3.10 (2H), 3.60-4.20 (18H), 6.80-7.00 (2H), 7.20 (3H)

Example 5

By the method shown below, the compound represented by the above formula (E) (in formula (E), m indicating the average degree of polymerization is 4.5 and n indicating the average degree of polymerization is 4.5) was obtained. Hereinafter, the compound represented by the above formula (E) is referred to as Compound (E).

4.85 g of Compound (E) was obtained in the same manner as in Example 3, except that 1.14 g of allyl glycidyl ether was used instead of glycidyl phenyl ether to synthesize a compound represented by the following formula (15) as an intermediate.

[Chemical Formula 17]

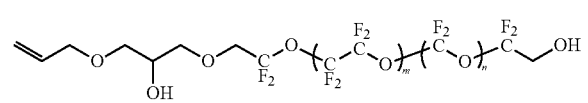

(15)

In the formula (15), m indicating the average degree of polymerization is 4.5, and n indicating the average degree of polymerization is 4.5.

$^1$H-NMR measurement of the obtained Compound (E) was performed, and the structure was identified by the following results.

$^1$H-NMR (CD$_3$COCD$_3$): δ[ppm]=2.20-2.30 (2H), 3.60-4.20 (18H), 5.10-5.30 (2H), 5.90 (1H), 7.20 (2H)

Example 6

By the method shown below, the compound represented by the above formula (F) (in the formula (F), m indicating the average degree of polymerization is 4.5 and n indicating the average degree of polymerization is 4.5) was obtained. Hereinafter, the compound represented by the formula (F) is referred to as Compound (F).

Glycerol diallyl ether was oxidized to synthesize an epoxy compound represented by the following formula (16). Then, Compound (F) was obtained in the same manner as in Example 3, except that an epoxy compound represented by the formula (16) was used instead of glycidyl phenyl ether in Example 3 to synthesize a compound represented by the following formula (17) as an intermediate.

[Chemical Formula 18]

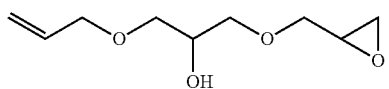

(16)

[Chemical Formula 19]

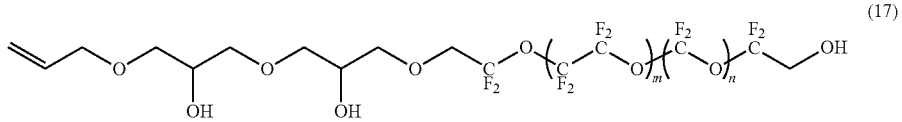

(17)

In the formula (17), m indicating the average degree of polymerization is 4.5, and n indicating the average degree of polymerization is 4.5.

$^1$H-NMR measurement of the obtained Compound (F) was performed, and the structure was identified by the following results.

$^1$H-NMR (acetone-D$_6$): δ [ppm]=2.20-2.30 (2H), 3.60-4.20 (23H), 5.10-5.30 (2H), 5.90 (1H), 7.20 (2H)

Example 7

By the method shown below, the compound represented by the above formula (G) (in formula (G), m indicating the average degree of polymerization is 4.5 and n indicating the average degree of polymerization is 4.5) was obtained. Hereinafter, the compound represented by the above formula (G) is referred to as Compound (G).

Compound (G) was obtained in the same manner as in Example 3, except that 0.954 g of the compound represented by the above formula (10) was used instead of the compound represented by the above formula (8) in Example 3.

$^1$H-NMR measurement of the obtained Compound (G) was performed, and the structure was identified by the following results.

$^1$H-NMR (acetone-D$_6$): δ [ppm]=2.00 (3H), 3.30-3.40 (2H), 3.60-4.20 (16H), 5.90 (5H), 7.50 (1H)

Example 8

By the method shown below, the compound represented by the above formula (H) (in formula (H), m indicating the average degree of polymerization is 4.5, and n indicating the average degree of polymerization is 4.5) was obtained. Hereinafter, the compound represented by the formula (H) is referred to as Compound (H).

Compound (H) was obtained in the same manner as in Example 4, except that 0.954 g of the compound represented by the above formula (10) was used instead of the compound represented by the above formula (8) in Example 4.

$^1$H-NMR measurement of the obtained Compound (H) was performed, and the structure was identified by the following results.

$^1$H-NMR (acetone-D$_6$): δ [ppm]=2.00 (3H), 3.10-3.40 (4H), 3.60-4.20 (18H), 6.80-7.00 (2H), 7.20 (1H), 7.50 (1H)

Example 9

By the method shown below, the compound represented by the above formula (I) (in formula (I), m indicating the average degree of polymerization is 4.5 and n indicating the average degree of polymerization is 4.5) was obtained. Hereinafter, the compound represented by the above formula (I) is referred to as Compound (I).

Compound (I) was obtained in the same manner as in Example 5, except that 0.954 g of the compound represented by the above formula (10) was used instead of the compound represented by the above formula (8) in Example 5.

$^1$H-NMR measurement of the obtained Compound (1) was performed, and the structure was identified from the following results.

$^1$H-NMR (acetone-D$_6$): δ [ppm]=2.00 (3H), 3.30-3.40 (2H), 3.60-4.20 (18H), 5.10-5.30 (2H), 5.90 (1H), 7.50 (1H)

Example 10

By the method shown below, the compound represented by the above formula (J) (in formula (J), m indicating the average degree of polymerization is 4.5, and n indicating the average degree of polymerization is 4.5) was obtained. Hereinafter, the compound represented by the formula (J) is referred to as Compound (J).

Compound (J) was obtained in the same manner as in Example 6, except that 0.954 g of the compound represented by the above formula (10) was used instead of the compound represented by the above formula (8) in Example 6.

$^1$H-NMR measurement of the obtained Compound (J) was performed, and the structure was identified by the following results.

$^1$H-NMR (acetone-$D_6$): δ [ppm]=2.00 (3H), 3.30-3.40 (2H), 3.60-4.20 (23H), 5.10-5.30 (2H), 5.90 (1H), 7.50 (1H)

Example 11

By the method shown below, a compound represented by the above formula (K) (in formula (K), m indicating the average degree of polymerization is 4.5) was obtained. Hereinafter, the compound represented by the formula (K) is referred to as Compound (K).

Compound (K) was obtained in the same manner as in Example 9 except that 20.5 g of a fluoropolyether (number average molecular weight 1025, molecular weight distribution 1.1) represented by $HOCH_2CF_2CF_2O(CF_2CF_2CF_2O)_h$ $CF_2CF_2CH_2OH$ (wherein h indicating an average polymerization degree is 4.5) was used, instead of a fluoropolyether (number average molecular weight 1000, molecular weight distribution 1.1) represented by $HOCH_2CF_2O(CF_2CF_2O)_h$ $(CF_2O)_iCF_2CH_2OH$ (wherein h indicating an average polymerization degree is 4.5 and i indicating an average polymerization degree is 4.5) of Example 9.

[Chemical Formula 20]

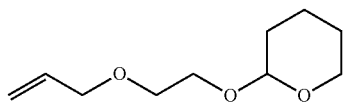
(18)

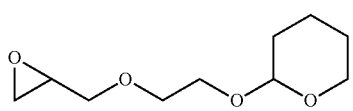
(19)

Then, in a 200 mL eggplant flask under a nitrogen atmosphere, 20 g of a fluoropolyether (number average molecular weight 1000, molecular weight distribution 1.1) represented by $HOCH_2CF_2O(CF_2CF_2O)_h(CF_2O)_i$ $CF_2CH_2OH$ (wherein h indicating an average degree of polymerization is 4.5 and i indicating an average degree of polymerization is 4.5), 1.59 g of the compound represented by the above formula (10), and 20 mL of t-butanol were charged and stirred at room temperature until uniform.

To this homogeneous solution, 0.67 g of potassium tert-butoxide was added, and the mixture was reacted by stirring at 70° C. for 14 hours. The resulting reaction product was cooled to 25° C., and transferred to a separatory funnel containing 30 mL of water. This was extracted with 100 mL of Vertrel XF. The organic layer was washed with water and further washed with saturated saline. The washed organic layer was dehydrated with anhydrous sodium sulfate. After the desiccant was filtered off, the filtrate was concentrated. The residue was purified by silica gel column chromatography to obtain the compound represented by the formula (20).

[Chemical Formula 21]

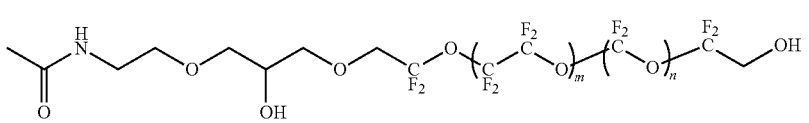
(20)

$^1$H-NMR measurement of the obtained Compound (K) was performed, and the structure was identified by the following results.

$^1$H-NMR (acetone-$D_6$): δ [ppm]=2.00 (3H), 3.30-3.40 (2H), 3.60-4.20 (18H), 5.10-5.30 (2H), 5.90 (1H), 7.50 (1H)

Example 12

By the method shown below, the compound represented by the above formula (L) (in formula (L), m indicating the average degree of polymerization is 4.5 and n indicating the average degree of polymerization is 4.5) was obtained. Hereinafter, the compound represented by the above formula (L) is referred to as Compound (L).

A compound represented by the following formula (18) was synthesized using ethylene glycol monoallyl ether, 3,4-dihydro-2H-pyran and p-toluenesulfonic acid. Furthermore, the epoxy compound represented by the following formula (19) was synthesized by oxidizing the compound represented by the formula (18) using metachloroperbenzoic acid.

In the formula (20), m indicating the average degree of polymerization is 4.5, and n indicating the average degree of polymerization is 4.5.

In a 200 mL eggplant flask under a nitrogen gas atmosphere, 5.80 g of the compound represented by the above formula (20), 1.21 g of the compound represented by the above formula (19), and 50 mL of t-butanol were charged and stirred at room temperature until uniform.

To this homogeneous solution, 0.112 g of potassium tert-butoxide was added, and the mixture was reacted by stirring at 70° C. for 20 hours. The obtained reaction product was cooled to 25° C. And then, 5 mL of hydrochloric acid methanol solution containing 1 mol/L hydrochloric acid in methanol was added, and the reaction product was stirred at room temperature for 1 hour. The reaction solution was transferred to a separatory funnel containing 60 mL of water, and was extracted with 100 mL of Vertrel XF. The organic layer was washed with water, and further washed with saturated saline. The organic washed organic layer was dehydrated with anhydrous sodium sulfate. After the desiccant was filtered off, the filtrate was concentrated. The residue was purified by silica gel column chromatography to obtain 3.82 g of Compound (L).

$^1$H-NMR measurement of the obtained Compound (L) was performed, and the structure was identified by the following results.

$^1$H-NMR (acetone-D$_6$): δ [ppm]=2.00 (3H), 3.35-3.45 (2H), 3.60-4.20 (20H), 7.50 (1H)

Comparative Example 1

A compound represented by the following formula (N) was synthesized by the method described in Patent Document 1.

[Chemical Formula 23]

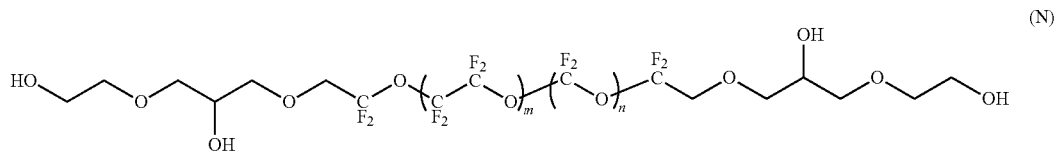

(N)

In the formula (N), m indicating the average degree of polymerization is 4.5, and n indicating the average degree of polymerization is 4.5.

Comparative Example 2

A compound represented by the following formula (O) having a non-chain organic group having an amide bond was synthesized by the method described in Patent Document 2.

[Chemical Formula 24]

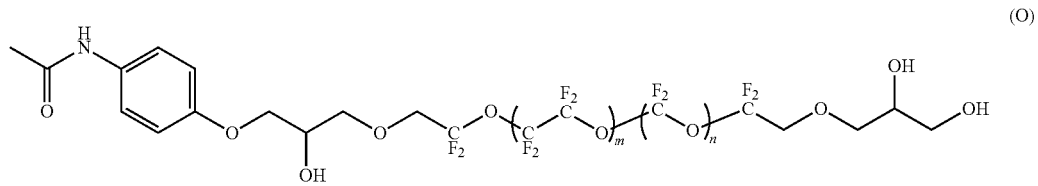

(O)

In the formula (O), m indicating the average degree of polymerization is 4.5, and n indicating the average degree of polymerization is 4.5.

The number average molecular weights of the compounds of Examples 1 to 12 and Comparative Examples 1 and 2 were determined by the above-described $^1$H-NMR and $^{19}$F-NMR measurements. The results are shown in Table 1.

TABLE 1

| Compound | | Number average molecular weight | Film thickness (Å) | Time Until Coefficient of Friction Sharply Increases (sec) | Si Adsorption amount |
|---|---|---|---|---|---|
| Example 1 | (A) | 1287 | 9.0 | 588 | 0.70 |
| Example 2 | (B) | 1315 | 9.1 | 579 | 0.74 |
| Example 3 | (C) | 1292 | 9.0 | 611 | 0.69 |
| Example 4 | (D) | 1326 | 9.2 | 639 | 0.68 |
| Example 5 | (E) | 1256 | 9.1 | 631 | 0.65 |
| Example 6 | (F) | 1330 | 9.2 | 669 | 0.61 |
| Example 7 | (G) | 1306 | 9.0 | 609 | 0.69 |
| Example 8 | (H) | 1340 | 9.0 | 610 | 0.67 |
| Example 9 | (I) | 1270 | 9.1 | 625 | 0.62 |
| Example 10 | (J) | 1344 | 9.2 | 672 | 0.62 |
| Example 11 | (K) | 1320 | 9.1 | 628 | 0.61 |
| Example 12 | (L) | 1274 | 9.0 | 710 | 0.55 |
| Comparative Example 1 | (N) | 1235 | 9.2 | 442 | 1.00 |
| Comparative Example 2 | (O) | 1279 | 9.0 | 491 | 0.87 |

Next, a lubricant layer-forming solution was prepared by using the compounds obtained in Examples 1 to 12 and Comparative Example 1 and Comparative Example 2 by the method described below. Then, using the obtained lubricant layer-forming solution, a lubricant layer of a magnetic recording medium was formed by the following method, and magnetic recording media of Examples 1 to 12 and Comparative Example 1 and Comparative Example 2 were obtained.

"Lubricant layer-forming solution" The compounds obtained in Examples 1 to 12 and Comparative Example 1 and Comparative Example 2 were each dissolved in Vertrel (registered trademark) XF (trade name, manufactured by Mitsui DuPont Fluoro Chemical Co., Ltd.), which is a fluorine-based solvent, and diluted with Vertrel so that the film thickness would be 9 Å to 10 Å when applied onto the protective layer, and a lubricant layer-forming solution of 0.001 to 0.01% by mass was obtained.

"Magnetic Recording Media"

A magnetic recording medium in which an adhesion layer, a soft magnetic layer, a first base layer, a second base layer, a magnetic layer, and a protective layer were sequentially provided on a 65 mm diameter substrate was prepared. The protective layer was made of carbon.

The lubricant layer-forming solutions of Examples 1 to 12 and Comparative Example 1 and Comparative Example 2 were applied by a dip method on the protective layer of the magnetic recording medium on which the layers up to the protective layer were formed.

Thereafter, the magnetic recording medium coated with the lubricant layer-forming solution was placed in a thermostatic chamber at 120° C. and subjected to heat treatment for 10 minutes. As a result, a lubricant layer was formed on the protective layer to obtain a magnetic recording medium.

The film thicknesses of the lubricant layers of the obtained magnetic recording media of Examples 1 to 12 and Comparative Example 1 and Comparative Example 2 were measured using FT-IR (trade name: Nicolet iS50, manufactured by Thermo Fisher Scientific). The results are shown in Table 1.

Also, wear resistance tests and chemical substance resistance tests were performed on the magnetic recording media of Examples 1 to 12 and Comparative Example 1 and Comparative Example 2 by the methods described below. The results are shown in Table 1.

(Wear Resistance Test)

Using a pin-on-disk type friction and wear tester, an alumina ball having a diameter of 2 mm was used as a contact and was slid on the lubricant layer of the magnetic recording medium with a load of 40 gf at a sliding speed of 0.25 m/sec, to measure a coefficient of friction of the surface of the lubricant layer. The sliding time until the coefficient of friction sharply increases was measured on the surface of the lubricant layer. The sliding time until the coefficient of friction sharply increases was measured four times for the lubricant layer of each magnetic recording medium, and an average value (time) thereof was used as an indicator of the wear resistance of the lubricant coating film.

The time until the coefficient of friction sharply increases can be used as an indicator of the wear resistance of the lubricant layer for the following reason. In the lubricant layer of the magnetic recording medium, wear progresses according to use of the magnetic recording medium. When the lubricant layer disappears due to wear, the contact and the protective layer are in direct contact with each other to cause the coefficient of friction to sharply increase.

As shown in Table 1, the magnetic recording media of Examples 1 to 12 have a longer sliding time until the coefficient of friction increases sharply than the magnetic recording media of Comparative Example 1 and Comparative Example 2, and have good wear resistance.

It is presumed that this is because in the compound represented by the formula (1) forming the lubricant layer in the magnetic recording media of Examples 1 to 12, at least one of $R^1$ and $R^5$ is an organic group having 1 to 8 carbon atoms wherein one or more hydrogen atoms of the organic group is substituted with a group having an amide bond, and $R^2$ and $R^4$ are divalent linkage groups having a polar group.

(Chemical Resistance Test)

The following evaluation method was used to examine the contamination of magnetic recording media with environmental substances that generate contaminants in a high temperature environment. In the following evaluation method, Si ions were used as the environmental substance, and the amount of Si adsorption was measured as the amount of contaminants that contaminate the magnetic recording medium and that were generated by the environmental substance.

Specifically, the magnetic recording medium to be evaluated was held for 240 hours in the presence of a siloxane-based Si rubber in a high-temperature environment at a temperature of 85° C. and a humidity of 0%. Next, the amount of Si adsorption existing on the surface of the magnetic recording medium was analyzed and measured using secondary ion mass spectrometry (SIMS), and the degree of contamination by Si ions was evaluated based on the amount of Si adsorption. The Si adsorption amount was evaluated using numerical values when the result of Comparative Example 1 was set to 1.00.

From Table 1, it is clear that the magnetic recording media of Examples 1 to 12 have a smaller amount of Si adsorption than the magnetic recording media of Comparative Example 1 and Comparative Example 2, and are not easily contaminated by environmental substances in a high temperature environment.

DESCRIPTION/EXPLANATION OF REFERENCES

10 . . . Magnetic recording medium,
11 . . . Substrate,
12 . . . Adhesion layer,
13 . . . Soft magnetic layer,
14 . . . First base layer,
15 . . . Second base layer,
16 . . . Magnetic layer,
17 . . . Protective layer,
18 . . . Lubricant layer.

The invention claimed is:

1. A fluorine-containing ether compound represented by the following formula (1),

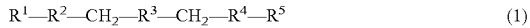

$$R^1-R^2-CH_2-R^3-CH_2-R^4-R^5 \quad (1)$$

wherein in the formula (1), $R^3$ is a perfluoropolyether chain; $R^2$ and $R^4$ are divalent linkage groups having a polar group and may be the same or different; $R^1$ and $R^5$ are bonded to an atom other than a carbon atom of $R^2$ or $R^4$; $R^1$ and $R^5$ are terminal groups composed of an organic group having 1 to 8 carbon atoms and may be the same or different; and at least one of $R^1$ and $R^5$ is a chain organic group having 1 to 8 carbon atoms wherein one or more hydrogen atoms of the chain organic group is substituted with a group having an amide bond.

2. The fluorine-containing ether compound according to claim 1, wherein the chain organic group is an alkyl group having 1 to 4 carbon atoms.

3. The fluorine-containing ether compound according to claim 1, wherein the polar group is a hydroxy group.

4. The fluorine-containing ether compound according to claim 1, wherein $R^2$ and $R^4$ in the formula (1) are represented by the following formula (2-1),

$$-(O-CH_2CH(OH)CH_2)_a-O- \quad (2\text{-}1)$$

wherein in the formula (2-1), a represents an integer of 1 to 3.

5. The fluorine-containing ether compound according to claim 1, wherein in the formula (1), $R^1$ is a chain organic group having 1 to 8 carbon atoms wherein one or more hydrogen atoms of the chain organic group are substituted with a group having an amide bond, and $R^5$ is an alkyl group in which one or more hydrogen atoms are substituted with a polar group.

6. The fluorine-containing ether compound according to claim 1, wherein in the formula (1), $R^3$ is any one of the following formulas (3) to (5), $$-CF_2O-(CF_2CF_2O)_c-(CF_2O)_d-CF_2- \quad (3)$$

wherein in the formula (3), c and d represent an average degree of polymerization and each represents 0 to 20, provided that c or d is 0.1 or more, $$-CF(CF_3)-(OCF(CF_3)CF_2)_e-OCF(CF_3)- \quad (4)$$

wherein in the formula (4), e represents an average degree of polymerization and represents 0.1 to 20, $$-CF_2CF_2-(OCF_2CF_2CF_2)_f-OCF_2CF_2- \quad (5)$$

wherein in the formula (5), f represents an average degree of polymerization and represents 0.1 to 20.

7. The fluorine-containing ether compound according to claim 1, wherein a number average molecular weight is in the range of 500 to 10,000.

8. A lubricant for magnetic recording media comprising the fluorine-containing ether compound according to claim 1.

9. A magnetic recording medium in which at least a magnetic layer, a protective layer, and a lubricant layer are sequentially provided on a substrate, wherein the lubricant layer contains the fluorine-containing ether compound according to claim 1.

10. The magnetic recording medium according to claim 9, wherein an average film thickness of the lubricant layer is 0.5 nm to 2 nm.

* * * * *